United States Patent [19]

Chupakhin et al.

[11] Patent Number: 5,166,348
[45] Date of Patent: Nov. 24, 1992

[54] BORNYL AND ISOBORNYL ESTERS OF CARBOXYLIC ACIDS OF CONDENSED TETRAHYDROQUINOXALINES

[75] Inventors: Oleg N. Chupakhin; Valery N. Charushin; Galina M. Petrova; Mikhail G. Ponizovsky; Vasily G. Baklykov, all of Sverdlovsk; Gunar Y. Dubur; Egils A. Biseniex, both of Riga; Yan R. Uldrikis, Elgava; Oleg U. Kiselev, Leningrad; Vera I. Ilienko, Leningrad; Vitaly G. Platonov, Leningrad; Valentina M. Guseva, Leningrad, all of U.S.S.R.

[73] Assignees: Uralsky politekhnichesky institut, Sverdlovsk, Russian Federation; Institut organicheskogo sinteza AN Latvii, Riga, Latvia

[21] Appl. No.: 730,897

[22] PCT Filed: Dec. 3, 1990

[86] PCT No.: PCT/SU90/00256

§ 371 Date: Aug. 5, 1991

§ 102(e) Date: Aug. 5, 1991

[87] PCT Pub. No.: WO91/08209

PCT Pub. Date: Jun. 13, 1991

[30] Foreign Application Priority Data

Dec. 4, 1989 [SU] U.S.S.R. .............................. 4765184

[51] Int. Cl.$^5$ ................. C07D 513/04; C07D 513/14; C07D 491/048
[52] U.S. Cl. ........................................ 544/345; 544/9; 544/343
[58] Field of Search ................. 544/345, 343

[56] References Cited

FOREIGN PATENT DOCUMENTS 1384590 3/1988 U.S.S.R. .............................. 544/343

*Primary Examiner*—Mark L. Berch
*Attorney, Agent, or Firm*—Keck, Mahin & Cate

[57] ABSTRACT

Bornyl and isobornyl esters of carboxylic acids of condensed tetrahydroquinoxalines having the general formula

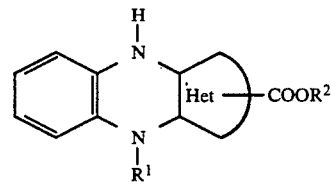

where $R^1$ is $CH_3$ or $C_2H_5$

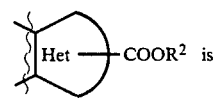

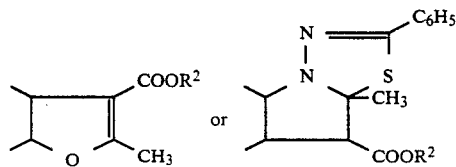

where $R^2$ is

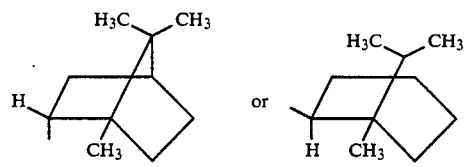

The proposed compounds are active against viruses and can therefore be used in medicine.

2 Claims, No Drawings

BORNYL AND ISOBORNYL ESTERS OF CARBOXYLIC ACIDS OF CONDENSED TETRAHYDROQUINOXALINES

FIELD OF THE ART

This invention relates to organic chemistry, and more particularly it relates to new compounds, bornyl and isobornyl esters of carboxylic acids of condensed tetrahydroquinoxalines having antiviral properties.

PRIOR ART

Known in the prior art are derivatives of 3a, 4, 9,9a-tetrahydrofuro (2,3a-b) quinoxaline (O. N. Chupakhin, V. N. Charushin, A. I. Chernyshev, "Application of $^1$H, $^{13}$C and $^{15}$N NMR in the Chemistry of 1,4-Diazines", Progress in Nuclear Magnetic Resonance Spectroscopy, Oxford; Pergamon Press, 1988, vol. 20 (2), pp. 177-184. However, the compound are not effective against viruses.

DISCLOSURE OF THE INVENTION

The proposed compounds are novel and have not been described in the literature.

The object of the invention is to provide new compounds having high antiviral activity and low toxicity.

The object is accomplished by provision of new compounds, which, according to the invention, are bornyl and isobornyl esters of carboxylic acids of condensed tetrahydroquinoxalines of the general formula:

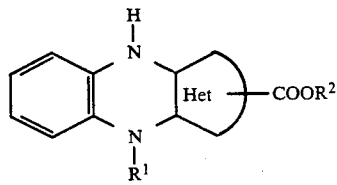
(I)

where: $R^1 = CH_3$; $C_2H_5$;

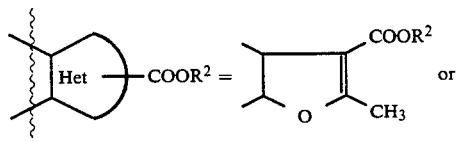

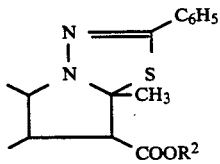

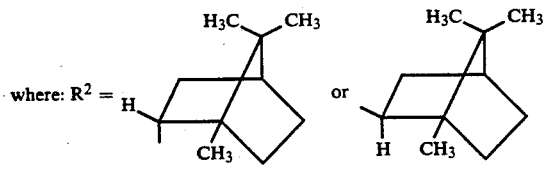

The proposed compounds have low toxicity and are active against influenza virus A and B. The most active compound, according to the invention, is isobornyl ester of 2,9-dimethyl-3a,4,9,9a-tetrahydrofuro 2,3-b quinoxaline-3-carboxylic acid of the formula

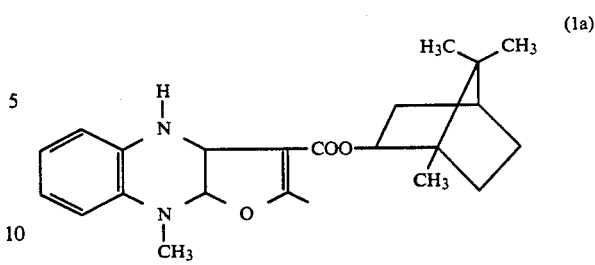
(1a)

Said compound has a broad spectrum of antiviral activity, i.e., it is highly active against tick-borne encephalitis virus, epidemic strains of influenza virus A, B and C resistant to remantadine, and also against the agent causing respiratory syncytial infection.

Best Mode of Carrying Out the Invention

The proposed new compounds-bornyl and isobornyl esters of carboxylic acid of condensed tetrahydroquinoxalines are colorless crystals readily soluble in chloroform and dimethylsulphoxide, moderately soluble in ethyl ether and ethyl alcohol, and sparingly soluble in water.

The structure of the proposed compounds was confirmed by the findings of elemental analysis and $^1$H NMR spectroscopy. The proposed compounds are active against viruses. The antiviral activity of the proposed compounds was studied on experimental animals.

The activity of the proposed compounds against influenza virus A and B was tested. The following compounds were tested:

isobornyl ester of 2,9-dimethyl-3a,4,9,9a-tetrahydrofuro 2,3-b quinoxaline-3-carboxylic acid (compound 1a);

isobornyl ester of 2-methyl-9-ethyl-3a,4,9,9a-tetrahydrofuro [2,3-b] quinoxaline-3-carboxylic acid (compound 1b);

bornyl ester of 2-methyl-9-ethyl-3a,4,9,9a-tetrahydrofuro [2,3-b] quinozaline-3-carboxylic acid (compound 1c);

bornyl ester of 3a,5-dimethyl-2-phenyl-3a,4, 4a,5,10,-10a-hexahydro-1,3,4-thiadiazole [2,3-a] quinoxaline (2,3-d) pyrrole-4carboxylic acid (compound 1d);

isobornyl ester of 3a,5-dimethyl-2-phenyl-3a,4, 4a,5,10,-10a-hexahydro-1,3,4-thiadiazole [2,3-a] quinoxaline [2,3-d]-pyrrole-4-carboxylic acid (compound 1e).

The proposed compounds were compared with the known antivirus drugs remantadine and adapromine.

The antiviral activity of the compounds was studied on chick embryos and albino mice infected with the virus.

The studies and estimation of efficacy of the compounds were performed according to the known procedure.

Experiments were carried out on 3 groups of animals (or embryos): test group (the virus and the proposed compounds were given), control group (the virus and distilled water or a 0.9% sodium chloride solution were given) and the group for comparison (the virus and the known antiviral compounds remantadine or adapromine were given).

The virus was given intransally to mice under a mild ether anaesthesia. The antiviral compounds were given per os a in dose of 1 mg per animal.

The results of the test are given in Tables 1 through 5.

TABLE 1

Studies on the Antiviral Activity of the Proposed Compound 1a in Experiments on Mice Infected with Influenza Virus A and B Compared with the Known Drugs Remantadine, Adapromine and Control.

| | Mice infected with influenza virus | | | | | |
|---|---|---|---|---|---|---|
| | influenza virus A | | | influenza virus B | | |
| Indices | compound 1a | remantadine | control | compound 1a | adapromine | control |
| 1 | 2 | 3 | 4 | 5 | 6 | 7 |
| % of diseased mice and of died mice | 27 | 13 | 77 | 20 | 20 | 74 |
| Factor of reduction of number of diseased mice (protection factor) | 2.8 | 6.0 | — | 3.7 | 3.7 | — |
| Efficiency, % | 64 | 83 | — | 73 | 73 | — |
| Activity of compound | +++ | ++++ | — | +++ | +++ | — |
| Mean incubation period, days | 9.7 | 10.0 | 8.0 | 11.0 | 10.9 | 8.6 |
| Elongation of animals life in test group compared with control, days | 1.6 | 2.8 | — | 2.4 | 2.3 | — |

TABLE 2

Studies on Antiviral Activity of Compound 1b in Experiments on Mice Infected with Influenza virus A and B (Compared with the Known Drugs Remantadine, Adapromine and Control)

| | Mice infected with influenza virus A and B | | | | | |
|---|---|---|---|---|---|---|
| | influenza virus A | | | influenza virus B | | |
| Indices | compound 1b | remantadine | control | compuond 1b | adapromine | control |
| 1 | 2 | 3 | 4 | 5 | 6 | 7 |
| % of diseased mice and of died mice | 47 | 5 | 73 | 27 | 20 | 75 |
| Factor of reduction of number of diseased mice (protection factor) | 1.6 | 14.6 | — | 2.9 | 3.8 | — |
| Efficiency, % | 37 | 93 | — | 65 | 74 | — |
| Activity of compound | + | ++++ | — | +++ | +++ | — |
| Mean incubation period, days | 9.2 | 11.7 | 7.7 | 10.0 | 10.3 | 7.9 |
| Elongation of animals life in test group compared with control, days | 2.1 | 4.0 | — | 2.2 | 2.4 | — |

TABLE 3

Studies of Antiviral Activity of the Proposed Compound 1c in Experiments on Mice Infected with Influenza Virus A and B (Compared with the Known Drugs Remantadine and Adapromine, and Control)

| | Mice infected with influenza virus A and B | | | | | |
|---|---|---|---|---|---|---|
| | influenza virus A | | | influenza virus B | | |
| Indices | compound 1c | remantadine | control | compound 1c | adapromine | control |
| 1 | 2 | 3 | 4 | 5 | 6 | 7 |
| % of diseased mice and of died mice | 43 | 15 | 69 | 25 | 25 | 70 |
| Factor of reduction of number of diseased mice (protection factor) | 1.6 | 14.6 | — | 2.8 | 2.8 | — |

TABLE 3-continued

Studies of Antiviral Activity of the Proposed Compound 1c in Experiments on Mice Infected with Influenza Virus A and B (Compared with the Known Drugs Remantadine and Adapromine, and Control)

| | Mice infected with influenza virus A and B | | | | | |
|---|---|---|---|---|---|---|
| | influenza virus A | | | influenza virus B | | |
| Indices 1 | compound 1c 2 | remantadine 3 | control 4 | compound 1c 5 | adapromine 6 | control 7 |
| Efficiency, % | 37 | 85 | — | 64 | 64 | — |
| Activity of compound | + | ++++ | — | +++ | +++ | — |
| Mean incubation period, days | 10.0 | 11.7 | 9.0 | 11.0 | 11.1 | 8.6 |
| Elongation of animals life in test group compared with control, days | 1.0 | 2.7 | — | 2.4 | 2.5 | — |

TABLE 4

Studies on Antiviral Activity of Compounds 1d and 1e in Experiments on Mice Infected with Influenza Virus B (Compared with Adapromine and Control)

| | Mice infected with influenza virus B | | | |
|---|---|---|---|---|
| Indices 1 | proposed 1d 2 | compound 1e 3 | adapromine 4 | control 5 |
| % of diseases mice and died mice | 20 | 21 | 12 | 72 |
| Factor of reduction of number of diseased mice (protection factor) | 3.6 | 3.4 | 6.0 | — |
| Efficiency, % | 72 | 71 | 83 | — |
| Activity of compounds | +++ | +++ | ++++ | — |
| Mean incubation period, days | 11.0 | 10.9 | 11.6 | — |
| Elongation of animals life in test group, days | 2.5 | 2.4 | 3.1 | — |

TABLE 5

Results of Studies on Antiviral Activity of Proposed Compounds 1a through 1e in Experiments on Mice Infected with Influenza Virus A and B

| | | Influenza virus A | | Influenza virus B | |
|---|---|---|---|---|---|
| Nos 1 | Compound 2 | Efficiency, % 3 | Activity 4 | Efficiency, % 5 | Activity 6 |
| 1. | Proposed compound 1a | 64 | +++ | 73 | +++ |
| 2. | Proposed compound 1b | 37 | + | 65 | +++ |
| 3. | Proposed compound 1c | 37 | + | 64 | +++ |
| 4. | Proposed compound 1d | — | | 72 | +++ |
| 5. | Proposed compound 1e | — | | 71 | +++ |

It can be seen from the Tables 1 through 5 that all proposed compounds are active against influenza virus B. The proposed compounds 1a through 1c are also active against influenza virus A. Compound 1a is especially effective (isobornyl ester of 2,9-dimethyl-3a,4,9a-tetrahydrofuro[2,3-d]quinozaline-3-carboxylic acid). The antiviral properties of compound 1a were studied in detail.

It was shown in experiments on chick embryos and albino mice that compound 1a has marked antiviral activity, it inhibits reproduction of influenza virus types A and B and saves mice infected with the virus.

The results of the tests are given in Tables 6 and 7.

TABLE 6

Results of Testing Antiviral Activity of Compound 1a in Experiments on Mice Infected with Influenza Virus A and B (the drug was given to mice in a dose of 1 mg/mouse, 24 hours and 1 hour before infection and in 24, 48 and 72 hours after infection)

| | Mice infected with influenza virus | | | | | |
|---|---|---|---|---|---|---|
| | influenza virus A | | | Influenza virus B | | |
| Indices 1 | compound 1a 2 | remantadine 3 | control 4 | compound 1a 5 | remantadine 6 | control 7 |
| % of diseased mice and died mice | 27 | 13 | 77 | 20 | 20 | 74 |
| Protection factor | 2.8 | 6.0 | — | 3.7 | 3.7 | — |
| Efficiency, % | 64 | 83 | — | 73 | 73 | — |
| Activity | +++ | ++++ | — | +++ | +++ | — |
| Mean Incubation | 9.7 | 10.0 | 8.0 | 11.0 | 10.9 | 8.6 |

TABLE 6-continued

Results of Testing Antiviral Activity of Compound 1a in
Experiments on Mice Infected with Influenza Virus A and B
(the drug was given to mice in a dose of 1 mg/mouse, 24 hours and
1 hour before infection and in 24, 48 and 72 hours after infection)

| | Mice infected with influenza virus | | | | | |
|---|---|---|---|---|---|---|
| | influenza virus A | | | Influenza virus B | | |
| Indices | compound 1a | remantadine | control | compound 1a | remantadine | control |
| 1 | 2 | 3 | 4 | 5 | 6 | 7 |
| Elongation of animal life in test group (compared with control), day | 1.6 | 2.8 | — | 2.4 | 2.3 | — |

It can be seen from Table 6 that the activity of compound 1a is sufficiently high and commensurable with that of remantadine and adapromine (remantadine and adapromine are the most active known anti-influenza drugs).

Lower activity of the proposed drug 1a against influenza virus A compared with remantadine can probably be compensated by enlargement of the dose because the toxicity of the proposed drug is 2.5-3 times lower than that of remantadine (see Table 7).

TABLE 7

Chemotherapeutic Index of Compound 1a Compared with
that of Remantadine and Adapromine

| | | Toxicity for mice | Minimum effective dose (mg/mouse) against influenza viruses | | Chemotherapeutic index for influenza viruses | |
|---|---|---|---|---|---|---|
| Nos | Drug | (mg/mouse) | type A | type B | type A | type B |
| 1 | 2 | 3 | 4 | 5 | 6 | 7 |
| 1. | Proposed compound 1a | 16 | 0.2 | 0.04 | 80 | 400 |
| 2. | Remantadine | 6 | 0.1 | — | 60 | — |
| 3. | Adapromine | 6 | — | 1.0 | — | 6 |

Table 7 shows that compound 1a has very high chemotherapeutic index for influenza virus A (about 80) and virus B (about 400) which is substantially higher than those of remantadine and adapromine.

The efficiency of compound against influenza viruses A and B is 60-70%. The compound is effective as a preventive means as well when administered 24 and 1 hour before infection or given in 24, 48 and 72 hours after infection. It is also effective as a therapeutic means.

The activity of the proposed compound 1a against influenza virus C has been studied. Experiments were performed on chick embryos because this virus does not propagate in the lungs of mice. The results are given in Table 8. They show that the compound inhibits reproduction of influenza virus C.

TABLE 8

Results of Testing Antiviral Activity of proposed
Compound 1a in Experiments on Chick Embryos Infected
with Influenza Virus C

| | Titre of virus (lg) in embryo treated with | | Inhibition of virus |
|---|---|---|---|
| Influenza virus C strains | compound 1a | solvent (control) | reproduction (lg) |
| 1 | 2 | 3 | 4 |
| C(USA)1233/47 | 2.8 ± 0.4 | 4.5 ± 0.3 | 1.7 |
| C(Leningrad)412/83 | 3.5 ± 0.3 | 5.0 ± 0.3 | 1.5 |
| C(Ulan-Ude)131/86 | 3.6 ± 0.3 | 5.2 ± 0.4 | 1.6 |
| C(Leningrad)393/87 | 3.2 ± 0.3 | 4.5 ± 0.3 | 1.3 |

The effect of the proposed compound 1a on morbidity and mortality of young mice borne from females infected with the virus was studied.

It was shown that the proposed compound 1a given to pregnant or nursing mice protects the sucklings from trasnplacental infection with the virus or infection from a diseased mouse.

The results of the test are given in Tables 9, 10 and 11.

Table 9 shows the results of the experiment where the activity of the proposed compound was estimated by mortality rate. Table 10 shows that the administration of the proposed compound 1a to infected mice protects their nurslings from infection and death; moreover, it promotes their normal growth as estimated by gain in weight. Table 10 shows that the weight of sucklings borne from infected female mice, which were given compound 1a, almost does not differ from the weight of young mice borne from control mice. Administration of compound 1a promotes an asymptomatic course of infection in pregnant mice and formation of immunity in their posterity that protects them from influenza during the first days of life.

Table 11 gives the results of the experiment in which neonate mice borne from infected females were infected with the influenza virus. It can be seen from the Table that the mortality in the control group of young mice (borne from mice infected with the virus without administration of drugs) was much higher than among the mice borne from the animals to whom the virus and the proposed compound 1a were given.

TABLE 9

Mortality of Mice Borne from Infected Females

| | % of lethal cases among mice after infection of their mothers | | | | |
|---|---|---|---|---|---|
| Compound given to female mice | in 6 days | in 7 days | in 8 days | in 9 days | in 10 days |
| 1 | 2 | 3 | 4 | 5 | 6 |
| Compound 1a + virus | 3 | 10 | 10 | 10 | 13 |
| placebo + virus | 21 | 50 | 68 | 76 | 1000 |

TABLE 10

Growth of Mice Borne from Females Infected with Influenza Virus

| Compound given to mice | Mean weight of suckling mice, g days | | | | |
|---|---|---|---|---|---|
| | 0 | 3 | 5 | 7 | 9 |
| 1 | 2 | 3 | 4 | 5 | 6 |
| Control | 1.5 | 2.5 | 2.9 | 4.0 | 4.6 |
| Proposed compound 1a plus influenza virus | 1.5 | 2.6 | 3.4 | 3.4 | 3.6 |
| 9% sodium chloride solution + virus | 1.3 | 1.5 | 1.5 | 1.3 | all mice died |

TABLE 11

Effect of Influenza Infection in Pregnant Mice Treated with Compound 1a (intranasally) on Sensitivity of Neonates to a Lethal Dose of Influenza Virus

| Compound given to pregnant mice | Mortality rate among suckling mice, % days after infection | | | |
|---|---|---|---|---|
| | 4 | 7 | 8 | 11 |
| 1 | 2 | 3 | 4 | 5 |
| Proposed compound 1a + influenza virus | 0 | 7 | 23 | 23 |
| 9% sodium chloride solution + virus | 44 | 88 | 100 | 100 |

The sensitivity to the proposed compound 1a of influenza virus strains resistant to remantadine was studied. The experiments were carried out on chick embryos that were infected into the chorionallantois.

Remantadine and the proposed compound 1a were given in a dose of 1 mg/embryo.

The embryos infected with influenza virus A were incubated for 48 hours at a temperature of 34° C. The presence of the virus in the embryo was determined by inhibition of haemaglutination. The virus titres were counted by Read and Mench. For estimation of the sensitivity of influenza virus strains to the studied compounds, the titre difference was determined (in units of $EID_{50}$, embryo intective dose) in controls and test embryos. Some virus strains that are resistant or only slightly sensitive to remantadine were sensitive to the proposed compound 1a. The results of the tests are given in Tables 12 and 13.

TABLE 12

Studies on Sensitivity of Influenza Virus A to Remantadine and Proposed Compound 1a (in a dose of 1 mg/embryo)

| Influenza virus A strains | Virus titres (lg $EID_{50}$) | | | Titre difference in control and experiment (lg $EID_{50}$) | |
|---|---|---|---|---|---|
| | control | remantadine | proposed compound | remantadine | proposed compound 1a |
| 1 | 2 | 3 | 4 | 5 | 6 |
| A(Moscow) 2848/86/H3N2/ | 8.0 | 6.75 | 4.5 | 1.25 | 3.5 |
| A(Moscow) 2813/86/H3N2/ | 7.25 | 5.5 | 4.75 | 1.75 | 2.5 |
| A(Riga) 9951/86/H3N2/ | 6.0 | 4.75 | 4.5 | 1.25 | 1.5 |
| A(Moscow) 2878/86/H3N2/ | 8.2 | 7.5 | 4.0 | 0.7 | 4.2 |
| A(Leningrad) 23/81/HON1/ | 4.75 | 4.5 | 3.0 | 0.25 | 1.75 |
| A(Victoria) 35/72/H3N2/ | 6.25 | 6.0 | 4.0 | 0.25 | 2.25 |

TABLE 13

Studies on Antiviral Activity of Proposed Compound 1a in Experiments on Chick Embryos Infected with Influenza Virus A Strains Resistant to Remantadine

| Strain | Index | substance given | | |
|---|---|---|---|---|
| | | proposed compound 1a | remantadine | solvent (control) |
| 1 | 2 | 3 | 4 | 5 |
| A(Leningrad) 23/81/HON1/ | % of embryos with virus | 0 | 57.1 | 62.5 |
| | efficiency, % | 90 | 0 | — |
| | activity | ++++ | | |
| A(Victoria) 35/73/H3N2/ | % of embryos with virus | 16.6 | 72.7 | 91.6 |
| | efficiency, % | 84 | 20 | — |
| | activity | ++++ | | |
| A(Moscow) 2879/86/H3N2/ | % of embryos with virus | 0 | 66.7 | 88.9 |
| | efficiency, % | 90 | 24 | — |
| | activity | ++++ | | |

Activity of the proposed compound 1a to the agent causing respiratory syncytial infection was tested. In experiments on tissue culture L-41 the proposed compound inhibits reproduction of RS virus (strain Novoshakhtinsky 3030). When given intranasally to infected cotton rats the proposed compound decreases the virus reproduction in the lungs of the animals; the man titre of the virus in the treated rats was 1.8–2.0 lg lower than in control group of animals. The results of the experiment are illustrated in Table 14.

TABLE 14

Effect of Proposed Compound 1a on Reproduction of RS Virus (strain Novoshakhtinsky 3080) in L-41 Tissue Culture

| Indices | Substance added to tissue culture | |
|---|---|---|
| | compound 1a | 0.9% NACl solution |
| 1 | 2 | 3 |
| % of test tubes with degenerated culture | 17 | 90 |
| Intensity of reduction of quantity of test tubes with degenerated cultures | 0.18 | 2.2 |
| Factor of reduction of quantity of test tubes with degenerated cultures | 5.3 | |
| Efficiency, % | 81 | |
| Activity | ++++ | |

The studies of the compound 1a revealed antiviral activity of the compound against the causative agent of tick-borne encephalitis.

Experiments were carried out on mongrel albino mice weighing 16–18 g.

The mice divided into two groups, the test and the control one, each of 15 mice. The virus of tick-borne encephalitis (Absettar strain) was given subcutaneously to the animals in both groups. 4 hours before infection, and also in 24, 48, 72 and 96 hours after infection, the animals in the test group were given 0.2 ml of a 0.5% solution of compound 1a in a 0.9% NaCl solution, with an additive of Tween-80 (into the stomach through a gastric tube). The mice in the control group were given 0.2 ml of the 0.9% aqueous solution of sodium chloride.

The mortality of mice in both groups was studied until the animals stopped dying.

The results of the experiments are given in Table 15. They show that the mortality rate decreases significantly if the mice were treated with the proposed compound 1a (from 62.5% in the control group to 18.7% in the test group, i.e. 3.3 times less). Thus, the proposed compound 1a is highly active against the causative agent of tick-borne encephalitis.

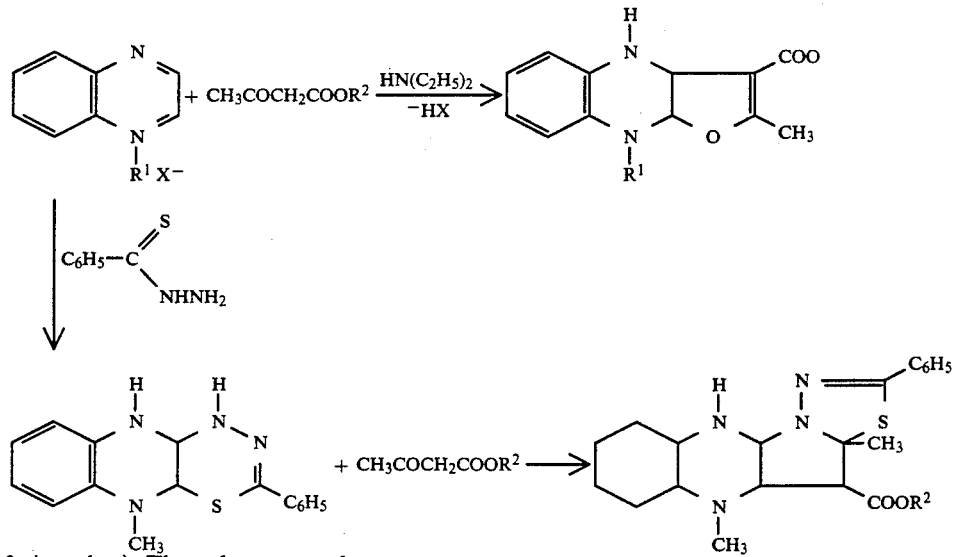

TABLE 15

Studies on Antiviral Activity of Proposed Compound 1a in Experiments on Mice Infected with tick borne Encephalitis Virus (Absettar strain)

| Indices | Substance given to mice | |
|---|---|---|
| | Compound 1a | Physiological saline solution (control) |
| % of diseased mice and mice which died | 18.7 | 62.5 |
| Factor of reduction of quantity of diseased mice (protective factor) | 3.3 | — |
| Efficiency, % | 70 | — |
| Activity of compound 1a | ++++ | — |
| Mean incubation period, days | 11.4 | 9.9 |
| Elongation of animal life in group of treated animals, days | 1.5 | — |

Acute toxicity of the proposed compounds 1a through 1e was tested in experiments on mongrel albino mice with oral administration of the drug. The compounds given in doses from 800 to 2000 mg/kg of body weight weight did not cause death. The LD$_{50}$ of remantadine was 640 mg/kg, and that of adapramine, 45 mg/kg.

The proposed compounds were tested for their effect on the mutagenic activity. The results of the tests showed the absence of mutagenic activity in the proposed compounds.

Thus, the experiments show that the proposed compounds have low toxicity and they are active against influenza virus A and B. The compound 1a has the most pronounced effect against the virus of the tick-borne encephalitis, epidemic, influenza viruses A, B and C, including those resistant to remantadine, and also the virus causing respiratory syncytial infection.

The proposed compounds are manufactured by the reaction between 1-alkylquinoxalinium or 10-methyl-2-phenyl-1,4,4a,5,10,10a-hexahydro-1,3,4-thidiazine [5,6-b] quinoxaline and bornyl or isobornyl ester of acetoacetic acid in the medium of an organic solvent. The synthesis of the proposed compounds is carried out by the following scheme:

pps where: $R^1 = CH_3, C_2H_5$; and $R^2$ is bornyl or isobornyl.

For a better understanding of the invention, the following examples of its practical embodiment are given by way of illustration.

EXAMPLE 1

To a mixture of 5 g (0.018 mol) of N-methylquinoxalinium iodide and 5 ml (0.021 mol) of isobornyl acetoacetate in 15 ml of ethyl alcohol added with stirring were 5 ml (0.05 mol) of diethylamine. The starting salt of quinoxaline was dissolved and the temperature of the reaction mixture rose to 40°–50° C. In 15 minutes, the reaction mixture was cooled on ice and passed through a filter to separate colorless crystals. The obtained product, weighing 6.2 g, was isobornyl ester of 2,9-dimethyl-3a,4,9,9a-tetrahydrofuro [2,3-b] quinoxaline-3-carboxylic acid (compound 1a). The yield was 88.6% of theoretical.

A sample of analytical purity was prepared by recrystallization from hexane; the melting point of the product was 144°–145° C. (with decomposition).

Found: %: C 71.6; H 7.9; N 7.3; $C_{23}H_{30}N_2O_3$. Calculated, %: C 72.2; H 7.9; N 7.3.

$^1$H NMR spectrum in deuterochloroform, δ, (ppm): 0.8–1.1 m, 1.4–2.0 m and 4.6–4.9 m (18H, isobornyl residue); 2.10 d (3H, CH$_3$); 3.07 s (3H, CH$_3$); 4.96 dd (1H, CH); 5.53 bs (1H, NH), 5.82 d (1H,CH); 6.4–6.9 m (4H, C$_6$H$_4$).

EXAMPLE 2

To a mixture of 5 g (0.018 mol) of N-ethylquinoxalinium iodide and 5 ml (0.021 mol) of isobornyl acetoacetate in 15 ml of ethyl alcohol added with stirring were 5 ml (0.05 mol) of diethylamine. The starting salt of quinoxaline was dissolved and the temperature of the reaction mixture rose to 40°–50° C. In 15 minutes, the reaction mixture was cooled in ice and colorless crystals of isobornyl 2-methyl-9-ethyl-3a,4,9,9a-tetrahydrofuran [2,3-b] quinoxaline-3-carboxylate (compound 1b) were separated on a filter. The yield of the product was 6 g which was 88% of theoretical. The sample of analytical purity was obtained by recrystallization from hexane. The melting point of the product was 132°–133° C. (with decomposition).

Found, %: C 73.3; H 8.2; N 7.2. $C_{24}H_{32}N_2O_3$. Calculated, %: C 72.9; H 7.9; N 7.1.

$^1$H NMR spectrum in deuterochloroform, δ (ppm):0.8–1.1 m. 1.4–20 m and 4.6–4.9 m (18H, isobornyl residue); 1.35 t (3H, $CH_3$); 2.14 d (3H, $CH_3$); 3.58 g (2H, $CH_2$); 4.60 bs (1H, NH); 5.00 dd (1H, CH); 5.96 d (1H, CH); 6.4–6.9 m (4H, $C_6H_4$).

EXAMPLE 3

To a mixture of 5 g (0.018 mole) of N-ethylquinoxalinium iodide and 5 ml (0.021 mole) of bornyl acetoacetate in 15 ml of ethyl alcohol added were 5 ml (0.05 mole) of diethylamine. The starting salt was dissolved and the temperature of the reaction mixture rose to 40°–50° C. The mixture was allowed to stand for an hour and the precipitated colorless crystals of bornyl-2-methyl-9-ethyl-3a,4,9,9a-tetrahydrofuro [2,3-b] quinoxaline-3-carboxylate (compound 1c) were separated on the filter. The sample of analytically pure product was obtained by recrystallization from hexane. The yield of the end product was 5.4 g, which was 78% of theoretical. Melting point—121° C. (with decomposition).

Found, C 72.3; H 8.1; N 6.8. $C_{24}H_{34}N_2O_3$. Calculated, in %: C 72.7; H 8.1; N 7.1.

$^1$H NMR spectrum in deuterochloroform, δ, (ppm): 0.8–1.0 m, 1.0–2.5 m and 4.9–5.2 m (18H, bornyl residue); 1.34 t (3H, $CH_3$); 2.11 d (3H, $CH_3$); 3.50 m (2H, $CH_2$); 4.55 b.s (1H, NH); 5.00 dd (1H, CH); 5.98 (1H, CH); 6.5–7.0 m (4H, $C_6H_4$).

EXAMPLE 4

To a suspension of 6 g (0.02 mole) of 10-methyl-2-phenyl-1,4,4a,5,10,10a-hexanhydro-1,3,4-thiadiaxine (5,6-b)quinoxaline in 100 ml of ethyl alcohol added were 4 g (0.02 mole) of bornyl acetoatetate. The reaction mixture was heated to 60°–70° C. and allowed to stand at this temperature for 30 minutes. The reaction mixture was then cooled to room temperature and allowed to stand overnight. The precipitated bornyl-3a,5-dimethyl-2-phenyl-3a,4,4a,5,10,10a-hexahydro-1,3,4-thiadiazole [2,3-a] quinoxaline (2,3-d) pyrrole-4-carboxylate (compound 1d) was separated on a filter and recrystallized from ethyl alcohol. The yield of the product was 6.5 g which was 65% of theoretical. The product was a colorless crystalline substance melting at 162°–163° C.

Found, %: C 68.8; H 7.1; N 10.9; S 6.4. $C_{29}H_{36}N_4O_2S$. Calculated, %: C 69.0; H 7.2; N 11.1; S 6.4.

$^1$H NMR spectrum in deuterochloroform, δ (ppm): 0.8–2.1 m and 4.8–5.0 m (18H, bornyl residue); 2.16 s (3H, $CH_3$); 3.05 s (3H, $CH_3$); 3.37 d (1H, CH); 4.30 bs (1H, H); 4.38 dd (1H, CH) 5.02 bs (1H, CH); 6.5–6.9 m (4H, $C_6H_4$); 7.2–7.9 m ($C_6H_5$).

EXAMPLE 5

To a suspension of 6 g (0.02 mole) of 10-methyl-2-phenyl-1,4,4a,5,10,10a-hexahydro-1,3,4-thiadiazine (5,6-b] quinoxaline in 100 ml of ethyl alcohol added were 4 g (0.02 mole) of isobornyl acetoacetate. The reaction mixture was heated to 60°–70° C. and kept at this temperature for 30 minutes. The mixture was then cooled to room temperature and allowed to stand overnight. The precipitated isobornyl 3a,5-dimethyl-2-phenyl-3a,4-,4a,5,10,10a-hexahydro-1,3,4-thiadiazole [2,3-a] quinoxaline [2,3-d]-pyrrole-4-carboxylate (compound 1e) was separated on a filter and recrystallized from ethyl alcohol. The yield of the product was 6.5 g, which was 65% of theoretical. The product was a crystalline substance melting at 167°–168° C.

Found, %: C 69.0; H 6.9; N 11.4; S 6.1. $C_{29}H_{36}N_4O_2S$. Calculated, %: C 69.0; H 7.2; N 11.1; S 6.4.

$^1$H NMR spectrum in deuterochloroform, δ (ppm): 0.8–2.0 m and 4.5–4.9 m (18H, isobornyl residue); 2.05 s (3H, $CH_3$); 3.20 d (1H, CH); 2.98 s (3H, $CH_3$); 4.22 b.s (1H, NH); 4.39 dd (1H, CH); 5.02 b.d (1H, CH); 6.4–6.8 m (4H, $C_6H_4$); 7.2–7.8 m (5H), $C_6H_5$).

Industrial Applicability

The proposed new compounds, bornyl and isobornyl esters of carboxylic acids of condensed tetrahydroquinoxolines are active against influenza viruses types A, B and C, tick-borne encephalities virus and the virus causing respiratory syncytial infection. Said new compounds can be used in medicine as the active principle of medicinal preparations.

We claim:

1. Bornyl and isobornyl esters of carboxylic acids of condensed tetrahydroquinoxalines having the formula

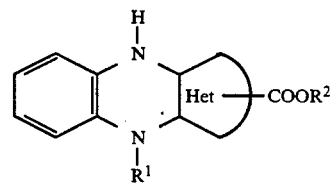

wherein: $R^1 = CH_3$; $C_2H_5$;

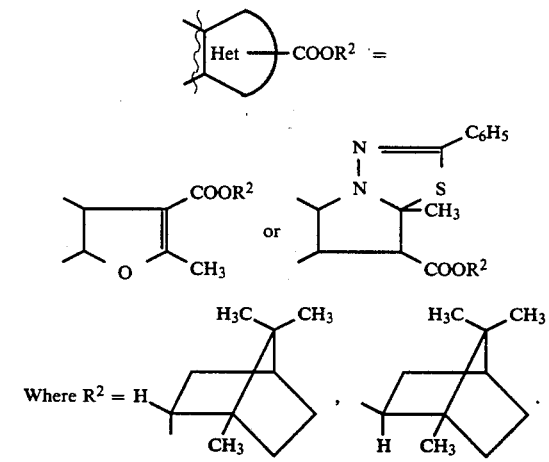

2. Isobornyl ester of 2,9-dimethyl-3a,4,9,9a-tetrahydrofuro 2,3-b quinoxaline-3-carboxylic acid with the following formula

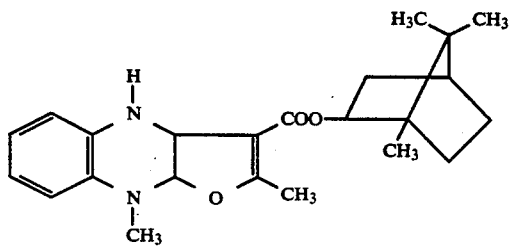

as claimed in claim 1.

* * * * *